United States Patent [19]

Arcamone et al.

[11] Patent Number: 4,766,142

[45] Date of Patent: * Aug. 23, 1988

[54] POLY-4-AMINOPYRROLE-2-CARBOXAMIDO DERIVATIVES AND THEIR USE AS ANTIUIRAL OR ANTITUMOR AGENTS

[75] Inventors: Federico Arcamone, Nerviano; Nicola Mongelli; Sergio Penco, both of Milan, all of Italy

[73] Assignee: Farmitalia Carlo Erba S.r.l., Milan, Italy

[*] Notice: The portion of the term of this patent subsequent to Apr. 19, 2005 has been disclaimed.

[21] Appl. No.: 783,588

[22] Filed: Oct. 3, 1985

[30] Foreign Application Priority Data

Jul. 16, 1985 [GB] United Kingdom ............... 8517922

[51] Int. Cl.$^4$ ................... A61K 31/40; C07D 403/12; C07D 403/14; C07D 413/14
[52] U.S. Cl. .................................. 514/422; 548/215; 548/336; 548/348; 548/518; 514/25; 514/151; 514/256; 534/751; 536/6.4; 536/4.1; 544/333
[58] Field of Search ............... 548/518, 336, 348, 215; 514/422, 25, 151, 256; 534/751; 544/333; 536/6.4, 4.1

[56] References Cited

U.S. PATENT DOCUMENTS

| | | |
|---|---|---|
| 3,420,844 | 1/1969 | Arcamone et al. ................ 548/518 |
| 3,420,845 | 1/1969 | Arcamone et al. ................ 548/518 |
| 3,432,522 | 3/1969 | Preau ................................ 548/518 |

FOREIGN PATENT DOCUMENTS

| | | |
|---|---|---|
| 547128 | 10/1957 | Canada ............................... 548/518 |
| 557568 | 5/1958 | Canada ............................... 548/518 |
| 1421245 | 11/1965 | France . |
| 1004974 | 3/1964 | United Kingdom . |
| 1009797 | 8/1964 | United Kingdom . |
| 1061639 | 7/1965 | United Kingdom . |

OTHER PUBLICATIONS

Baker, et al., J. Am. Chem. Soc., (1985), v. 107, pp. 8266-8268.
F. Arcamone, "On Distamycin A and Related Compounds . . . ", Medicinal Chemistry, Milan, 1972, pp. 29-44.
P. Chandra, et al, "Some Structural Requirements for the Antibiotic . . . " Febs Letters, Jan. 1972, vol. 19, #4, pp. 327-330.
Waehnert, U. et al, "Dependent Inactivation of the DNA . . . " Chemical Abstracts, vol. 83, 1975, p. 252.
Zimmer; C. et al, "Binding of Analogs of the Antibiotics . . . " Chemical Abstracts, vol. 76, 1972, p. 180.
Nikitin, S. M. et al, "DNA Base Pair Sequence Specific Ligands . . . " Institute of Molecular Biology, Academy of Science of the USSR, Moscow, pp. 542-551.
Taylor, J. S. et al, "DNA Affinity Cleaving" Tetrahedron 40,3,457 (1984).
Schultz, P. G. et al, "Sequence Specific Double Strand Cleavage of DNA by Bis(EDTA-distamycinFC$^{II}$) and EDTA-Bis(distamycin)Fe$^{II}$" Am. Chem. Soc. 105,26,7748 (1983).
Arcamone, F., "On Distamycin and Related Compounds, Selective Antiviral Agents" Med. Chem. 1972, pp. 29-45.
Bialer, M. et al, "Structure-Activity Relationship . . . " Jour. of Med. Chem, 1979, vol. 22, No. 11, pp. 1296-1301.
Chandra, P. et al, "Some Structural Requirements for the Antibiotic Action of Distamycin" FEBS Letters, vol. 16, No. 4, Sep. 1971, pp. 249-252.
Kuroyedov, A. A. et al, "Distamycin A and its Analogs as Agents for Blocking of endo R. EcoRI Activity" Gene, 1 (1977) 389-395.
Arcamone, F. et al, "Structure and Synthesis of Distamycin A" Nature, Sep. 5, 1964 vol. 203, pp. 1064-1065.
Luck, G. et al, "Specific Interactions of Distamycin A . . . " Nucleic Acids Research, vol. 4, No. 8, Aug. 1977, pp. 2655-2671.
Kopka, M. L. et al, "The Molecular Origin of DNA—Drug Specificity . . . " Proc. Natl. Acad. Sci. USA vol. 82, pp. 1376-1380, Mar. 1985, Biochemistry.
Youngquist, R. S. et al, "Sequence-Specific Recognition . . . " Proc. Natl. Acad. Sci USA vol. 82, pp. 2565-2569, May 1985, Biochemistry.
Chemical Abstracts: 68:21767z, 68:21768a, 88:83397a, 88:201h, 97:215877e, 82:25984e, 99:176269c, 95:61898g, 89:102109x, 81:163162r, 100:39669h.
Chem. Abstracts: 84:150434t, 90:87174q, 88:50585g.
Chemical Abstracts: 68:87088k, 71:101629h, 71:101631c.
Chemical Abstracts: 79:38445t.
Chemical Abstracts: 77:14824y, 76:108639y, 76:149456e.
Penco, S. et al, "Distamicina A-Nota II . . . " Gazz. Chim. Ital.-97(1967) pp. 1110-1115.
Martinez, J., "Activated N-Nitrosocarbomates for . . . " J. Med. Chem 1982,25, pp. 178-182.
Grehn, L. "Synthesis and Antiviral Activity of Distamycin A. Analogues . . . ", J. Med. Chem. 1983, 26, 1042-1049.
Nikitin, S. M., "DNA Base Pair Sequence-specific Ligands . . . ", Chemical Abstracts, vol., 95, 1981, p. 32, 95:35304r.

Primary Examiner—Donald G. Daus
Assistant Examiner—William A. Teoli, Jr.
Attorney, Agent, or Firm—Murray and Whisenhunt

[57] ABSTRACT

Compound of the formula (I)

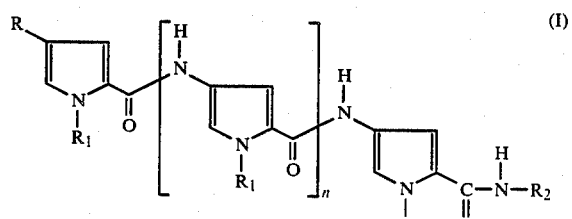

(Abstract continued on next page.)

wherein
n is zero or an integer of 1 to 3;
R is
(a) —NHR₃, wherein R₃ is
 (a') —CON(NO)R₄, in which R₄ is C₁-C₄ alkyl either unsubstituted or substituted by halogen; or
 (b') —CO(CH₂)ₘ—R₅, in which R₅ is halogen, oxiranyl, methyloxiranyl, aziridinyl, a group

or a group

and m is zero or an integer of 1 to 4; or
(b)

wherein either R₆ and R₇ are the same and are each oxiranemethyl, aziridinemethyl, or C₂-C₄ alkyl 2-substituted by halogen or by a group —OSO₂R₈ wherein R₈ is C₁-C₄ alkyl or phenyl, or one of R₆ and R₇ is hydrogen and the other is as defined above;

each group R₁ is, independently, hydrogen or C₁-C₄ alkyl;

R₂ is a C₁-C₆ alkyl group terminating with (i) a basic moiety chosen from an amino group, a mono- or di-C₁-C₆ alkylamino group, an amidino group, a group

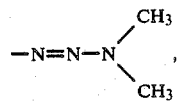

imidazolyl, imidazolinyl, tetrahydropyrimidinyl and oxazolidinyl; or (ii) a carboxy group; or (iii) a free hydroxy group —OH or a glycosilated hydroxy group —OD wherein D is a glucose, mannose or ribose sugar residue or the daunosamine amino-sugar residue; with the proviso that n is different from one when R₂ is

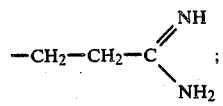

and the pharmaceutically acceptable salts thereof.
The compounds are useful as antiviral and antitumor agents.

6 Claims, No Drawings

POLY-4-AMINOPYRROLE-2-CARBOXAMIDO DERIVATIVES AND THEIR USE AS ANTIUIRAL OR ANTITUMOR AGENTS

The invention relates to poly-4-aminopyrrole-2-carboxamido derivatives, to a process for their preparation and to pharmaceutical compositions containing them.

Distamycin A is a well known compound having the following formula

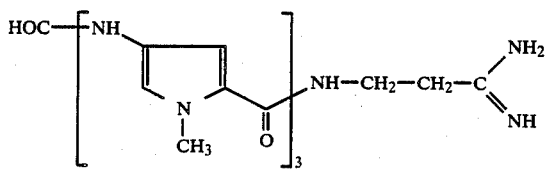

Literature referring to distamycin A includes, for example, Nature 203, 1064 (1964).

The invention provides distamycin A derivatives having the following general formula (I)

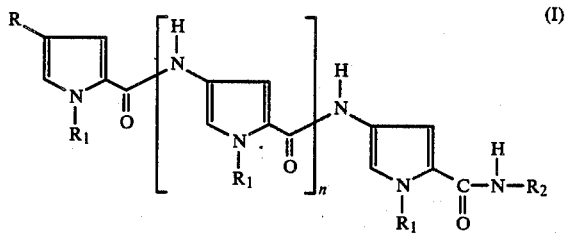

wherein
n is zero or an integer of 1 to 3;
R is
(a) —NHR$_3$, wherein R$_3$ is
(a') —CON(NO)R$_4$, in which R$_4$ is C$_1$–C$_4$ alkyl either unsubstituted or substituted by halogen; or
(b') —CO(CH$_2$)$_m$—R$_5$, in which R$_5$ is halogen, oxiranyl, methyloxiranyl, aziridinyl, cyclopropyl or an alicyclic α,β-unsaturated ketone or lactone, and m is zero or an integer of 1 to 4; or
(b)

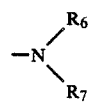

wherein either R$_6$ and R$_7$ are the same and are each oxiranemethyl, aziridinemethyl, or C$_2$–C$_4$ alkyl 2-substituted by halogen or by a group —OSO$_2$R$_8$, wherein R$_8$ is C$_1$–C$_4$ alkyl or phenyl, or one of R$_6$ and R$_7$ is hydrogen and the other is as defined above;
each group R$_1$ is, independently, hydrogen or C$_1$–C$_4$ alkyl;
R$_2$ is a C$_1$–C$_6$ alkyl group terminating with a basic or acidic moiety or with a free or glycosilated hydroxy group, with the proviso that n is different from one when R$_2$ is

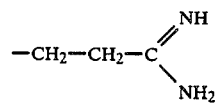

The invention includes also the pharmaceutically acceptable salts of the compounds of formula (I) as well as all the possible isomers covered by the formula (I), both separately and in mixture.

When R$_4$ is unsubstituted C$_1$–C$_4$ alkyl, methyl and ethyl are preferred, in particular methyl.

When R$_4$ is C$_1$–C$_4$ alkyl substituted by halogen, the halogen is, preferably, chlorine or bromine; in this case preferred R$_4$ values are chloroethyl and fluoroethyl.

Preferred n values are zero, 1 and 2.

When R$_5$ is halogen, it is, preferably, chlorine or bromine.

When R$_5$ is methyloxiranyl, it may be either 2-methyloxiranyl

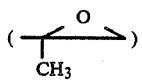

or 3-methyloxiranyl

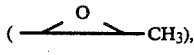

preferably being 3-methyloxiranyl.

When R$_5$ is an alicyclic α,β-unsaturated ketone or lactone, it is, e.g., a group

or, respectively, a group

Preferred R$_5$ values are oxiranyl

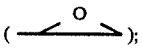

1-aziridinyl

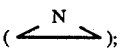

cyclopropyl

a group

or a group

Preferred m values are zero, 1 or 2.

A $R_6/R_7$ $C_2$–$C_4$ alkyl group 2-substituted by halogen is, preferably, 2-chloroethyl.

A $R_6/R_7$ $C_2$–$C_4$ alkyl group 2-substituted by a group —$OSO_2R_8$ is, preferably, a group —$CH_2$—$CH_2$—$OSO_2R_8$, wherein $R_8$ is $C_1$–$C_4$ alkyl, preferably methyl.

Preferably each group $R_1$, independently, is $C_1$–$C_4$ alkyl, in particular methyl and, most preferably, all groups $R_1$ are methyl. Subject to the above proviso, when $R_2$ is a $C_1$–$C_6$ alkyl group terminating with a basic moiety, the $C_1$–$C_6$ alkyl is, preferably, $C_1$–$C_4$ alkyl, in particular ethyl or n-propyl, and the basic moiety is, for instance, an amino group; a mono- or di-$C_1$–$C_6$ alkyl amino group, e.g. di-$C_1$–$C_4$-alkyl-amino; an amidino group; a group

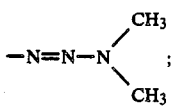

or a nitrogen containing heteromonocyclic ring such as, e.g., imidazolyl, imidazolinyl, tetrahydropyrimidinyl and oxazolidinyl. Preferred $R_2$ $C_1$–$C_6$ alkyl groups terminating with a basic moiety are, subject to the above proviso, e.g.,

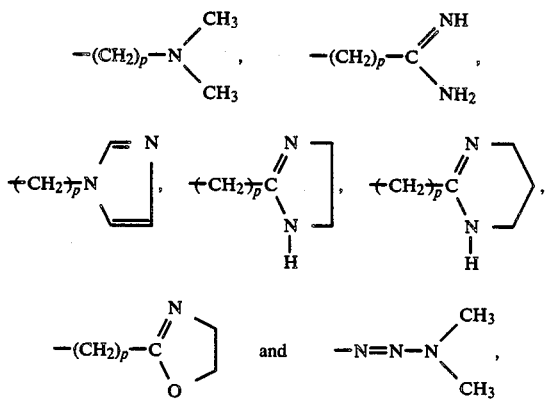

wherein p is an integer of 1 to 4.

When $R_2$ is a $C_1$–$C_6$ alkyl group terminating with an acidic moiety, the $C_1$–$C_6$ alkyl is preferably $C_1$–$C_4$ alkyl, in particular ethyl or n-propyl, and the acidic moiety is, preferably, a carboxy group.

Preferred $R_2$ $C_1$–$C_6$ alkyl group terminating with an acidic moiety is, e.g., a group —$(CH_2)_p$—COOH wherein p is an integer of 1 to 4.

When $R_2$ is a $C_1$–$C_6$ alkyl group terminating with a free hydroxy group it is, e.g., a group —$(CH_2)_p$—$CH_2OH$ wherein p is an integer of 1 to 4.

When $R_2$ is a $C_1$–$C_6$ alkyl group terminating with a glycosilated hydroxy group, it is, e.g., a group —$(CH_2)_p$—$CH_2$—O—D wherein p is as defined above and D is a sugar or amino-sugar residue.

The sugar residue may be, e.g., a glucose, mannose or ribose residue; the amino-sugar residue may be, for instance, daunosamine.

As already said, the invention includes also the pharmaceutically acceptable salts of the compounds of formula (I). The salts includes both the salts with pharmaceutically acceptable acids, either inorganic acids such as, e.g., hydrochloric, hydrobromic, nitric and sulfuric, or organic acids such as, e.g., citric, tartaric, maleic, fumaric, methanesulfonic and ethanesulfonic, and the salts with pharmaceutically acceptable bases, either inorganic bases such as, for instance, alkali metal, e.g. sodium or potassium, or alkaline-earth metal, e.g. calcium or magnesium, or zinc or aluminium, hydroxides, or organic bases, such as, e.g., aliphatic amines as methylamine, diethylamine, trimethylamine, ethylamine, and heterocyclic amines as, e.g., piperidine.

Salts of the compounds of formula (I) with acids may be, e.g., the salts of the compounds of formula (I) wherein $R_2$ is a $C_1$–$C_6$ alkyl group terminating with a basic moiety with an acid, e.g. one of those hereabove specified.

Salts of the compounds of formula (I) with bases may be, e.g., the salts of the compounds of formula (I) wherein $R_2$ is a $C_1$–$C_6$ alkyl group terminating with an acidic moiety with a base, e.g. one of those hereabove specified.

A preferred class of compounds under this invention is represented by the compounds of formula (I) wherein, subject to the above proviso, n is zero, 1 or 2;

R is —$NHR_3$ wherein $R_3$ is (a') —$CON(NO)R_4$ wherein $R_4$ is $C_1$–$C_4$ alkyl substituted by halogen, or (b') —$CO(CH_2)_m$—$R_5$ wherein $R_5$ is halogen, oxiranyl, 1-aziridinyl, cyclopropyl, or an alicyclic α,β-unsaturated lactone, and m is zero, 1 or 2;

each group $R_1$ is, independently, $C_1$–$C_4$ alkyl;

$R_2$ is a $C_1$–$C_6$ alkyl group terminating with a basic moiety, and the salts thereof with pharmaceutically acceptable acids, in particular with hydrochloric acid.

In the above preferred class a $R_4$ or $R_5$ $C_1$–$C_4$ alkyl group is, preferably, methyl or ethyl; a halogen atom is, preferably, chlorine; an alicyclic α,β-unsaturated lactone is, preferably, a group

a $R_1$ $C_1$–$C_4$ alkyl group is, preferably, methyl; in the $R_2$ substituent the $C_1$–$C_6$ alkyl group is, preferably, $C_1$–$C_4$ alkyl, in particular ethyl or n-propyl, and the basic terminal moiety may be of those previously specified in particular, e.g., a group

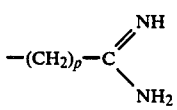

wherein p is an integer of 1 to 4.

A particularly preferred group of compounds in the ambit of the above preferred class are the compounds of formula (I) wherein, subject to the above proviso, n is zero, 1 or 2;

R is —NHR$_3$ wherein R$_3$ is (a') a group —CON(NO)R$_4$ wherein R$_4$ is —CH$_2$—CH$_2$—Cl, or (b') a group —CO(CH$_2$)$_m$—R$_5$ wherein either m is 1 or 2 and R$_5$ is chlorine, or m is zero and R$_5$ is oxiranyl, 1-aziridinyl or cyclopropyl, or m is 2 and R$_5$ is

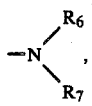

each group R$_1$ is methyl;

R$_2$ is a C$_1$-C$_4$ alkyl group with a basic terminal moiety chosen from amino, a di-C$_1$-C$_4$-alkyl-amino group and amidino, and the salts thereof with pharmaceutically acceptable acids, in particular hydrochloric acid.

In the hereabove said preferred group of compounds, preferred R$_2$ values are

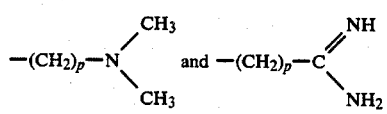

wherein p is an integer of 1 to 4.

Another preferred class of compounds under this invention are the compounds of formula (I) wherein, subject to the above proviso, n is zero, 1 or 2;

R is

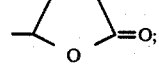

wherein R$_6$ and R$_7$ are the same and are each oxiranemethyl, 1-aziridinemethyl, or a C$_2$-C$_4$ alkyl group 2-substituted by halogen or by a group —O—SO$_2$R$_8$ wherein R$_8$ is C$_1$-C$_4$ alkyl;

each group R$_1$ is, independently, C$_1$-C$_4$ alkyl;

R$_2$ is a C$_1$-C$_6$ alkyl group terminating with a basic moiety, and the salts thereof with pharmaceutically acceptable acids, in particular with hydrochloric acid.

In the above preferred class a C$_2$-C$_4$ alkyl group in R$_6$/R$_7$ is, preferably, ethyl; a halogen is, preferably, chlorine; when R$_6$ and R$_7$ are a C$_2$-C$_4$ alkyl group 2-substituted by halogen, they are, preferably, 2-chloroethyl; when R$_6$ and R$_7$ are a C$_2$-C$_4$ alkyl 2-substituted by a group —OSO$_2$R$_8$ where R$_8$ is C$_1$-C$_4$ alkyl, they are, preferably, methanesulfonyloxyethyl; a C$_1$-C$_4$ alkyl group for R$_1$ is, preferably, methyl; in the R$_2$ substituent the C$_1$-C$_6$ alkyl group is, preferably, C$_1$-C$_4$ alkyl, in particular ethyl or n-propyl, and the terminal basic moiety, may be one of those previously specified, e.g., a group

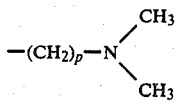

or a group

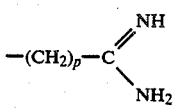

wherein p is an integer of 1 to 4.

A particularly preferred group of compounds within the hereabove said preferred class are the compounds of formula (I) wherein, subject to the above proviso, n is zero, 1 or 2;

R is

wherein R$_6$ and R$_7$ are both oxiranemethyl, 1-aziridinemethyl, 2-chloroethyl or methanesulfonyloxyethyl;

each group R$_1$ is methyl;

R$_2$ is a C$_1$-C$_4$ alkyl group with a terminal basic moiety chosen from amino, a di-C$_1$-C$_4$-alkylamino group and amidino, and the salts thereof with pharmaceutically acceptable acids, in particular with hydrochloric acid.

In the hereabove said preferred group of compounds preferred R$_2$ values are

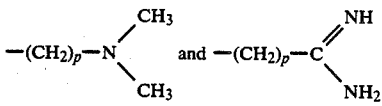

wherein p is an integer of 1 to 4.

Specific examples of preferred compounds under this invention, especially in the form of salts with hydrochloric acid, are the following:

β-[N-methyl-4-[N-methyl-4-(3-methyl-3-nitrosoureido)pyrrole-2-carboxamido]pyrrole-2-carboxamido]propionamidine;

β-[N-methyl-4-[N-methyl-4-[3-(2-chloroethyl)-3-nitrosoureido]pyrrole-2-carboxamido]pyrrole-2-carboxamido]propionamidine;

3-[N-methyl-4-[N-methyl-4-[3-methyl-3-nitrosoureido]-pyrrole-2-carboxamido]pyrrole-2-carboxamido]propyl-dimethylamine;

3-[N-methyl-4-[N-methyl-3-[3-(2-chloroethyl)-3-nitrosoureido]pyrrole-2-carboxamido]pyrrole-2-carboxamido]propyl-dimethylamine;

3-[N-methyl-4-[N-methyl-4-[N-methyl-4-(3-methyl-3-nitrosoureido)pyrrole-2-carboxamido]pyrrole-2-carboxamido]pyrrole-2-carboxamido]propyl-dimethylamine;

3-[N-methyl-4-[N-methyl-4-[N-methyl-4-[3-(2-chloroethyl)-3-nitrosoureido]pyrrole-2-carboxamido]pyrrole-2-carboxamido]pyrrole-2-carboxamido]propyl-dimethylamine;

N-deformyl-N-[N-methyl-4-(3-methyl-3-nitrosoureido)-pyrrole-2-carboxamido]Distamycin A;

N-deformyl-N-[N-methyl-4-[3-(2-chloroethyl)-3-nitrosoureido]pyrrole-2-carboxamido]Distamycin A;

3-[N-methyl-4-[N-methyl-4-[N-methyl-4-[N-methyl-4(3-methyl-3-nitrosoureido)pyrrole-2-carboxamido]-pyrrole-2-carboxamido]pyrrole-2-carboxamido]pyrrole-2-carboxamido]propyl-dimethylamine;

3-[N-methyl-4-[N-methyl-4-[N-methyl-4-[N-methyl-4[3-(2-chloroethyl)-3-nitrosoureido]pyrrole-2-carboxamido]pyrrole-2-carboxamido]pyrrole-2-carboxamido]pyrrole-2-carboxamido]propyl-dimethylamine;

β-[N-methyl-4-[N-methyl-4-(oxiranecarboxamido)pyrrole-2-carboxamido]pyrrole-2-carboxamido]propionamidine;

3-[N-methyl-4-[N-methyl-4-(oxiranecarboxamido)pyrrole-2-carboxamido]pyrrole-2-carboxamido]propyl-dimethylamine;

3-[N-methyl-4-[N-methyl-4-[N-methyl-4-(oxiranecarboxamido)pyrrole-2-carboxamido]pyrrole-2-carboxamido]pyrrole-2-carboxamido]propyl-dimethylamine;

N-deformyl-N-[N-methyl-4-(oxiranecarboxamido)pyrrole-2-carboxamido]Distamycin A;

3-[N-methyl-4-[N-methyl-4-[N-methyl-4-[N-methyl-4-(oxiranecarboxamido)pyrrole-2-carboxamido]pyrrole-2-carboxamido]pyrrole-2-carboxamido]pyrrole-2-carboxamido]propyl-dimethylamine;

β-[N-methyl-4-[N-methyl-4-(cyclopropylcarboxamido)pyrrole-2-carboxamido]pyrrole-2-carboxamido]propionamidine;

3-[N-methyl-4-[N-methyl-4-(cyclopropylcarboxamido)-pyrrole-2-carboxamido]pyrrole-2-carboxamido]propyl-dimethylamine;

3-[N-methyl-4-[N-methyl-4-[N-methyl-4-(cyclopropylcarboxamido)pyrrole-2-carboxamido]pyrrole-2-carboxamido]pyrrole-2-carboxamido]propyl-dimethylamine;

N-deformyl-N-[N-methyl-4-(cyclopropylcarboxamido(pyrrole-2-carboxamido]Distamycin A;

3-[N-methyl-4-[N-methyl-4-[N-methyl-4-[N-methyl-4-(cyclopropylcarboxamido)pyrrole-2-carboxamido]-pyrrole-2-carboxamido]pyrrole-2-carboxamido]pyrrole-2-carboxamido]propyl-dimethylamine;

β-[N-methyl-4-[N-methyl-4-(3-methyloxiranecarboxamido)pyrrole-2-carboxamido]pyrrole-2-carboxamido]propionamidine;

3-[N-methyl-4-[N-methyl-4-(3-methyloxiranecarboxamido)pyrrole-2-carboxamido]pyrrole-2-carboxamido]propyl-dimethylamine;

3-[N-methyl-4-[N-methyl-4-[N-methyl-4-(3-methyloxiranecarboxamido)pyrrole-2-carboxamido]pyrrole-2-carboxamido]pyrrole-2-carboxamido]propyl-dimethylamine;

N-deformyl-N-[N-methyl-4-(3-methyloxiranecarboxamido)pyrrole-2-carboxamido]Distamycin A;

3-[N-methyl-4-[N-methyl-4-[N-methyl-4-[N-methyl-4-(3-methyloxiranecarboxamido)pyrrole-2-carboxamido]pyrrole-2-carboxamido]pyrrole-2-carboxamido]pyrrole-2-carboxamido]propyl-dimethylamine;

β-[N-methyl-4-[N-methyl-4-(2-chloroethylcarboxamido)pyrrole-2-carboxamido]pyrrole-2-carboxamido]propionamidine;

3-[N-methyl-4-[N-methyl-4-(2-chloroethylcarboxamido)pyrrole-2-carboxamido]pyrrole-2-carboxamido]propyl-dimethylamine;

3-[N-methyl-4-[N-methyl-4-[N-methyl-4-(2-chloroethylcarboxamido)pyrrole-2-carboxamido]pyrrole-2-carboxamido]pyrrole-2-carboxamido]propyl-dimethylamine;

N-deformyl-N-[N-methyl-4-(2-chloroethylcarboxamido)pyrrole-2-carboxamido]Distamycin A;

3-[N-methyl-4-[N-methyl-4-[N-methyl-4-[N-methyl-4-(2-chloroethylcarboxamido)pyrrole-2-carboxamido]-pyrrole-2-carboxamide]pyrrole-2-carboxamido]pyrrole-2-carboxamido]propyl-dimethylamine;

β-[N-methyl-4-[N-methyl-4-[1-(aziridine)carboxamido]pyrrole-2-carboxamido]pyrrole-2-carboxamido]propionamidine;

3-[N-methyl-4-[N-methyl-4-[1-(aziridine)carboxamido]-pyrrole-2-carboxamido]pyrrole-2-carboxamido]propyl-dimethylamine;

3-[N-methyl-4-[N-methyl-4-[N-methyl-4-[1-(aziridine)-carboxamido]pyrrole-2-carboxamido]pyrrole-2-carboxamido]pyrrole-2-carboxamido]propyl-dimethylamine;

N-deformyl-N-[N-methyl-4-[1-(aziridine)carboxamido]-pyrrole-2-carboxamido]Distamycin A;

3-[N-methyl-4-[N-methyl-4-[N-methyl-4-[N-methyl-4-[1-(aziridine)carboxamdio]pyrrole-2-carboxamido]-pyrrole-2-carboxamido]pyrrole-2-carboxamido]pyrrole-2-carboxamido]propyl-dimethylamine;

β-[N-methyl-4-[N-methyl-4-[N,N-bis(2-chloroethylamino)]pyrrole-2-carboxamido]pyrrole-2-carboxamido]propionamidine;

3-[N-methyl-4-[N-methyl-4-[N,N-bis(2-chloroethylamino)]pyrrole-2-carboxamido]pyrrole-2-carboxamido]propyl-dimethylamine;

3-[N-methyl-4-[N-methyl-4-[N-methyl-4-[N,N-bis(2-chloroethylamino)]pyrrole-2-carboxamido]pyrrole-2-carboxamido]pyrrole-2-carboxamido]propyl-dimethylamine;

N-deformyl-N-[N-methyl-4-[N,N-bis(2-chloroethylamino)]pyrrole-2-carboxamido]Distamycin A;

3-[N-methyl-4-[N-methyl-4-[N-methyl-4[N-methyl-4-[N,N-bis(2-chloroethylamino)]pyrrole-2-carboxamido]pyrrole-2-carboxamido]pyrrole-2-carboxamido]pyrrole-2-carboxamido]propyl-dimethylamine.

The compounds object of the invention can be prepared by a process comprising:

(A) reacting a compound of formula (II)

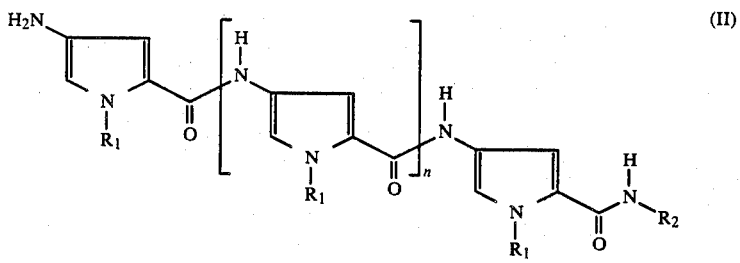
(II)

wherein
$R_1$, $R_2$ and n are as defined above, with a compound of formula (III)

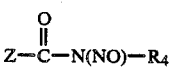
(III)

wherein
$R_4$ is as defined above and Z is a leaving group, so obtaining a compound of formula (I) wherein R is —$NHR_3$ and $R_3$ is —$CON(NO)R_4$, wherein $R_4$ is as defined above; or (B) reacting a compound of formula (II), wherein $R_1$, $R_2$ and n are as defined above, with a compound of formula (IV)

$$Z'\text{—CO—}(CH_2)_m\text{—}R_5 \quad (IV)$$

wherein
$R_5$ and m are as defined above and Z' is a leaving group, so obtaining a compound of formula (I) wherein R is —$NHR_3$ and $R_3$ is —$CO(CH_2)_m$—$R_5$, wherein m and $R_5$ are as defined above; or (C) reacting a compound of formula (II), wherein $R_1$, $R_2$ and n are as defined above, with a compound of formula (V)

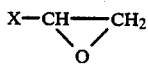
(V)

wherein
X may be hydrogen, $C_1$-$C_2$ alkyl or halomethyl, to give a compound of formula (VI)

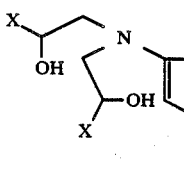
(VI)

wherein
$R_1$, $R_2$ and n are as defined above and each X has the meaning corresponding to the meaning of X in the compound (V), and transforming a compound of formula (VI) into a compound of formula (I) wherein R is

wherein $R_6$ and $R_7$ are as defined above; and, if desired, converting a compound of formula (I) into another compound of formula (I) and/or, if desired, salifying a compound of formula (I) or obtaining a free compound from a salt and/or, if desired, separating a mixture of isomers of formula (I) into the single isomers.

In the compounds of formula (III) the leaving group Z may be, e.g., an azido group or a trichlorophenoxy or succinimido-N-oxy group.

The reaction between a compound of formula (II) and a compound of formula (III) is preferably carried out in the presence of a solvent and, preferably, using an excess of the compound of formula (III), e.g. from about 1.1 to about 2 moles of compound (III) per 1 mole of compound (II). The solvent preferably is an inert organic solvent chosen e.g. from dialkylsulphoxides, e.g. dimethylsulphoxide, aliphatic acid dialkylamides, e.g. dimethylformamide or dimethylacetamide, phosphoric acid triamide or hexamethylphosphoramide, for example, dioxane or dimethoxyethane. Dimethylformamide (DMF) is a particularly preferred solvent.

The reaction temperature may range from about −10° C. to about 25° C., although 0° C. is a particularly preferred temperature.

The time required for the reaction may vary within the range from about 0.5 to about 6 hours.

The displaceable group Z' in the compound of formula (IV) may be, e.g., a halogen atom, e.g. chlorine or bromine, or an imidazolyl or phenoxy group.

The reaction between a compound of formula (II) and a compound of formula (IV) is preferably carried out in the presence of a solvent and, preferably, using an excess of the compound of formula (IV), e.g. from about 1.1 to about 2 moles of compound (IV) per 1 mole of compound (II).

The solvent preferably is an inert organic solvent chosen from dialkylsulfoxides, e.g. dimethylsulfoxides, aliphatic acid dialkylamide, e.g., dimethylformamide, heterocyclic amines like pyridine, aliphatic alcohols and also water.

A particularly preferred solvent is DMF.

The reaction temperature may range from about −50° C. to about 50° C. The time required for the reaction may vary approximately within the range from 0.5 to 24 hours.

When in the compound of formula (V) X is halomethyl, it is preferably, chloromethyl or bromomethyl.

The reaction between a compound of formula (II) and a compound of formula (V) is preferably carried out in the presence of a solvent and, preferably, using an excess of the compound of formula (V), e.g. from about 25 moles to about 50 moles of compound (V) per 1 mole of compound (II).

The solvent can be, e.g., water, an aliphatic alcohol, e.g. methanol or ethanol, an aliphatic carboxylic acid such as, e.g., acetic acid, an aliphatic acid dialkylamide, e.g. dimethylformamide, or a dialkylsulphoxide, e.g. dimethylsulphoxide, dioxane or dimethoxyethane. Methanol is a particularly preferred solvent.

The reaction temperature may range from about −20° C. to about 25° C.

The time required for the reaction may vary within the range from about 2 to about 48 hours.

The transformation of a compound of formula (VI) into a compound of formula (I) wherein R is a group

wherein $R_6$ and $R_7$ are as previously defined, may be carried out through reactions commonly used in the organic chemistry.

Thus, for example, a compound of formula (VI) wherein each group X is hydrogen or $C_1$–$C_2$ alkyl may be reacted with an halogenating agent such as, e.g., an halide, e.g. chlorine or bromine, or a thionyl halide, e.g. thionylchloride, to give a compound of formula (I) wherein R is a group

wherein each $R_6$ and $R_7$ is $C_2$–$C_4$ alkyl 2-substituted by halogen, e.g. chlorine or bromine. Similarly, a compound of formula (VI) wherein X is hydrogen or $C_1$–$C_2$ alkyl may be reacted with a sulfonic acid of formula $R_8SO_3H$, wherein $R_8$ is as defined above or, most preferably, with a reactive derivative thereof such as, e.g., the corresponding sulfonyl halide, e.g. chloride, or anhydride, to give a compound of formula (I) wherein R is a group

wherein each $R_6$ and $R_7$ is $C_2$–$C_4$ alkyl 2-substituted by a group $-O-SO_2R_8$ wherein $R_8$ is as defined above.

On the other hand, a compound of formula (VI) wherein each group X is halomethyl, e.g. chloromethyl or bromomethyl may be reacted with a base to give a compound of formula (I) wherein R is a group

wherein each $R_6$ and $R_7$ is oxiranemethyl.

The base may be either an inorganic base such as, for instance, an alkali metal, e.g. sodium or potassium, hydroxide, or an alkaline-earth metal, e.g. calcium or magnesium, hydroxide, or an organic base such as, for instance, an aliphatic amine, e.g. trimethylamine, or a heterocyclic amine, e.g. pyridine, piperidine, morpholine or methylmorpholine.

Other compounds of formula (I) wherein R is a group

may be prepared from a compound of formula (VI) through reactions well known in the organic chemistry and following known procedures.

Also the optional conversion of a compound of formula (I) into another compound of formula (I), the salification of a compound of formula (I) and the preparation of a free compound from a salt may be carried out according to known methods.

Conventional procedures, such as, e.g., fractional crystallization and chromatography, may also be used for the optional separation of a mixture of isomers of formula (I) into the single isomers.

The compound of formula (II) can be prepared by following known procedures, for example procedures analogous to those described for preparing distamycin derivatives in Gazz. Chim. Ital. 97, 1110 (1967).

In particular, for example, a compound of formula (II) may be obtained by the following steps:
(1) reaction of a compound of formula (VII)

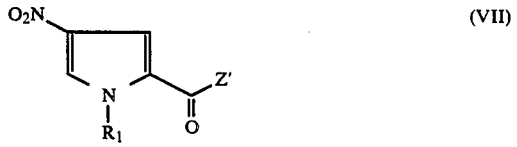

wherein
$R_1$ and $Z'$ are as defined above, with a compound of formula (VIII)

$$H_2N-R_2 \quad \text{(VIII)}$$

wherein
$R_1$ is as defined above, to obtain a compound of formula (IX)

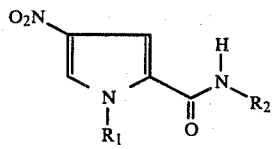

wherein
$R_1$ and $R_2$ are as defined above;
(2) catalytic hydrogenation of an obtained compound of formula (IX) to obtain a compound of formula (X)

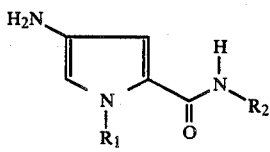

wherein
$R_1$ and $R_2$ are as defined above;
(3) reaction of a compound of formula (VII) with a compound of formula (X) to obtain a compound of formula (XI)

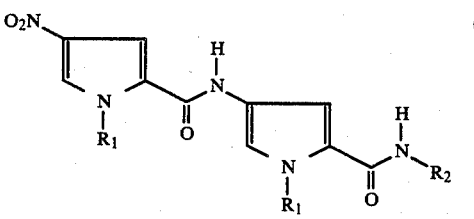

wherein
$R_1$ and $R_2$ are as defined above; and
(4) catalytic hydrogenation of a compound of formula (XI) to obtain a compound of formula (XII)

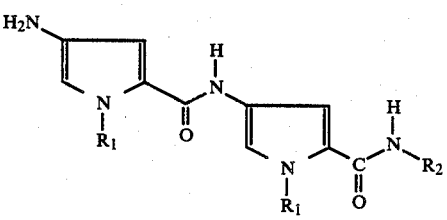

wherein
$R_1$ and $R_2$ are as defined above.

A compound of formula (XII) corresponds to a compound of formula (II) wherein n is zero; in order to obtain a compound of formula (II) wherein n is 1, a compound of formula (XI) can be further processed through the steps (2) and (3) indicated above and so on.

Compounds of formula (III) are known compounds and they can be prepared, for example, according to J. Med. Chem. (1982), 25, 178–182.

Compounds of formula (IV) and (V) are known compounds too or may be prepared by known methods from known compounds.

In particular, for instance, compounds of formula (IV) are either commercial compounds or can be prepared through activation of the carboxy parent compounds in a conventional way.

Compounds of formula (V) are commercially available compounds.

The compounds of the invention can be used as antiviral and antineoplastic agents.

They show, e.g., a remarkable effectiveness in interfering with the reproductive activity of the pathogenic viruses and protect tissue cells from viral infections. For example they show activity against DNA viruses such as, for instance, Herpes, e.g. *Herpex simplex* and *Herpes zoster*, viruses, and Adenoviruses, and against retroviruses such as, for instance, Sarcoma viruses, e.g., Murine sarcoma virus, and Leukemia viruses, e.g. Friend leukemia virus.

The compounds of the invention show also cytostatic properties towards tumor cells.

Owing to the above activity the compounds of the invention are able, e.g., to inhibit the growth of various tumors, for instance breast carcinoma and tumors induced by viruses, e.g. Maloney Sarcoma virus.

The compounds of the invention can be administered by the usual routes, for example parenterally, e.g. by intravenous injection or infusion, intramuscularly, subcutaneously, or also topically.

The dosage depends on the age, weight and conditions of the patient and on the administration route.

For example, a suitable dosage for administration to adult humans may range from about 0.1 to about 100 mg pro dose 1–4 times a day.

As already said, the invention includes also pharmaceutical compositions containing a compound of formula (I) as the active substance, in association with one or more pharmaceutically acceptable excipients.

The pharmaceutical compositions of the invention are usually prepared following conventional methods and are administered in a pharmaceutically suitable form.

For instance, solutions for intravenous injection of infusion may contain as carrier, for example, sterile water or preferably they may be in the form of sterile aqueous isotonic saline solutions.

Suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride. In the forms for topical application, e.g. creams, lotions or pastes for use in dermatological treatment, the active ingredient may be mixed with conventional oleaginous or emulsifying excipients.

The following examples illustrate but do not limit the invention.

The abbreviations DMF and THF stand for N,N-dimethylformamide and, respectively, tetrahydrofurane.

EXAMPLE 1

To a stirred aqueous solution of N,N-dimethylaminopropylamine (2.03 g in 40 ml of water) and sodium bicarbonate (3.36 g) at room temperature a solution of N-methyl-4-n-nitropyrrole-2-carboxylic acid chloride (4 g) in 5 ml of benzene was added. The resulting mixture was stirred for 2 hours at room temperature, saturated with sodium chloride and extracted with benzene (2×50 ml). The dried organic extracts were concentrated in vacuo and the residue was crystallized from light petroleum ether to yield 3.5 g of pure 3-[N-methyl-4-nitro-pyrrole-2-carboxamido]propyldimethylamine, white needles, m.p. 118°–120° C.

N.M.R. (DMSO-d$_6$): δ 1.60 (2H, m); 2.12 (6H, s); 3.23 (2H, t); 3.20 (2H, m); 3.88 (3H, s); 7.37 (1H, d); 8.08 (1H, bd); 8.35 (1H, bt).

EXAMPLE 2

The compound of example 1 (3.4 g) was dissolved in ethanol (40 ml) and diluted hydrochloric acid (20 ml) and reduced over a Pd catalyst (5% on carbon) under H$_2$ pressure (50 psi) in a Parr apparatus. Water (20 ml) was added and the catalyst filtered off. The resulting solution was concentrated and the residue was dissolved in water (40 ml). Sodium bicarbonate (4 g) was added, followed by a solution of N-methyl-4-nitropyrrole-2-carboxylic acid chloride (2.8 g) in 20 ml of benzene. The resulting mixture was stirred for about 2 hours at room temperature and then was extracted with chloroform. The dried organic extracts were concentrated in vacuo and the residue was purified by column chromatography (CHCl$_3$ 75, EtOH$_{95\%}$ 25, NH$_4$OH 0.6) to give 4.7 g of 3-[N-methyl-4-(N-methyl-4-nitropyrrole-2-carboxamido)pyrrole-2-carboxamido]propyldimethylamine as a yellow solid, m.p. 178°–180° C.

N.M.R. (CDCl$_3$) δ: 1.74 (2H, m); 2.30 (6H, s); 2.49 (2H, t); 3.44 (2H, m); 3.88 (3H, s); 3.99 (3H, s); 6.58 (1H, d); 7.21 (1H, d); 7.38 (1H, d); 7.6 (1H, br); 8.80 (1H, bs).

By analogous procedure, the following compounds were obtained:

3-[N-methyl-4-[N-methyl-4-[N-methyl-4-nitropyrrole-2-carboxamido]pyrrole-2-carboxamido]pyrrole-2-carboxamido]propyl-dimethylamine, m.p. 175° C. (dec.);

N.M.R. (DMSO-d$_6$) δ: 1.63 (2H, m); 2.22 (6H, s); 2.38 (2H, t); 3.16 (2H, dt); 3.80 (3H, s); 3.85 (3H, s); 3.87 (3H, s); 3.97 (3H, s); 6.80–7,30 (6H, m); 7.59 (1H, d); 8.04 (1H, t); 8.16 (1H, d); 9.84 (1H, bs); 9.95 (1H, bs); 10.26 (1H, bs);

3-[N-methyl-4-[N-methyl-4-[N-methyl-4-[N-methyl-4-nitropyrrole-2-carboxamido]pyrrole-2-carboxamido]-pyrrole-2-carboxamido]pyrrole-2-carboxamido]propyl-dimethylamine, m.p. 195° C. (dec.);

N.M.R. (DMSO-d$_6$) δ: 1.64 (2H, m); 2.13 (6H, s); 2.27 (2H, t); 3.20 (2H, dt); 3.80 (3H, s); 3.85 (3H, s); 3.88 (3H, s); 3.98 (3H, s); 6.82 (1H, d); 7.04 (2H, m); 7.18 (1H, d); 7.26 (2H, d); 7.58 (1H, d); 8.18 (1H, d); 8.02 (1H, t); 9.86 (1H, s); 9.94 (1H, s); 10.25 (1H, s);

β-[N-methyl-4-[N-methyl-4-nitropyrrole-2-carboxamido]pyrrole-2-carboxamido]propionamidine hydrochloride;

β-[N-methyl-4-methyl-4-[N-methyl-4-nitropyrrole-2-carboxamido]pyrrole-2-carboxamido]pyrrole-2-carboxamido]propionamidine hydrochloride;

β-[N-methyl-4-[N-methyl-4-[N-methyl-4-[N-methyl-4-nitropyrrole-2-carboxamido]pyrrole-2-carboxamido]-pyrrole-2-carboxamido]pyrrole-2-carboxamido]propionamidine hydrochloride.

EXAMPLE 3

β-N-methyl-4-[N-methyl-4-nitropyrrole-2-carboxamido]pyrrole-2-carboxamido]propionamidine hydrochloride (900 mg) dissolved in 150 ml of ethanol, 75 ml of water and 9 ml of 2N HCl was hydrogenated in a Parr apparatus for 45 minutes at 45 psi of H$_2$ at room temperature over a Pd catalyst (10% on carbon). The catalyst was filtered off and the filtrate was evaporated under vacuum to yield 930 mg of crude β-[N-methyl-4-[N-methyl-4-aminopyrrole-2-carboxamido]pyrrole-2-carboxamido]propionamidine dihydrochloride. The residue was dissolved in methyl alcohol (60 ml), cooled to −20° C. and heated with 12 ml of ethylene oxide. After 15 minutes the temperature was allowed to rise and the mixture is left at room temperature overnight. The solution was evaporated to dryness affording, after chromatography on SiO$_2$ washed with HCl, 800 mg of pure β-[N-methyl-4-[N-methyl-4-[N,N-bis-(2-hydroxyethylamino)]pyrrole-2-carboxamido]pyrrole-2carboxamido]propionamidine hydrochloride;

Mass spectrum: m/e 419 (M$^+$); 420 (M$^+$ +1);

$^1$H-N.M.R. (dimethyl-d$_6$ sulfoxide), δ: 2.63 (2H, t); 2.90–3.80 (10H, m); 4.55 (2H, br); 6.30 (1H, d); 6.52 (1H, d); 6.92 (1H, d); 7.12 (1H, d); 8.20 (1H, t); 8.70 (2H, bs); 9.01 (2H, bs); 9.63 (1H, s);

U.V. (EtOH 95%): λ max 245, ε=16,352; λ max 292, ε=15,070.

By analogous procedure the following compounds were obtained:

N-deformyl-N-[N-methyl-4-[N,N-bis(2-hydroxyethylamino)]pyrrole-2-carboxamido]Distamycin A hydrochloride;

3-[N-methyl-4-[N-methyl-4-[N,N-bis(2-hydroxyethylamino)]pyrrole-2-carboxamido]pyrrole-2-carboxamido]propyldimethylamine hydrochloride;

3-[N-methyl-4-[N-methyl-4-[N-methyl-4-[N,N-bis(2-hydroxyethylamino)]pyrrole-2-carboxamido]pyrrole-2-carboxamido]pyrrole-2-carboxamido]propyl-dimethylamine hydrochloride;

3-[N-methyl-4-[N-methyl-4-[N-methyl-4-[N-methyl-4-[N,N-bis(2-hydroxyethylamino)]pyrrole-2-carboxamido]pyrrole-2-carboxamido]pyrrole-2-carboxamido]pyrrole-2-carboxamido]propyl-dimethylamine hydrochloride.

EXAMPLE 4

A stirred solution of β-[N-methyl-4-[N-methyl-4-[N,N-bis(2-hydroxyethylamino)]pyrrole-2-carboxamido]pyrrole-2-carboxamido]propionamidine hydrochloride (717 mg) in dry pyridine (10 ml) was cooled with an ice bath, treated under nitrogen atmosphere with a solution of methansulphonylchloride in pyridine (1.27M, 2.7 ml) and stirred at 5° C. for 45 minutes. After quenching with methyl alcohol, the whole was allowed to warm to room temperature and evaporated to dryness. The crude product was chromatographed on silica yielding 440 mg of β-[N-methyl-4-[N-methyl-4-[N,N-bis(2-chloroethylamino)]pyrrole-2-carboxamido]pyrrole-2-carboxamido]propionamidine hydrochloride.

$^1$H-NMR (dimethyl-d$_6$sulfoxide), δ 2.63 (t, 2H); 3.30–3.80 (m, 10H); 3.78 (s, 3H); 3.81 (s, 3H); 6.42 (d, 1H); 6.55 (d, 1H); 6.92 (d, 1H); 7.17 (d, 1H); 8.20 (t, 1H); 8.70 (bs, 2H); 9.02 (bs, 2H); 9.68 (s, 1H); U.V. (EtOH 95%): λmax 245, ε=17,373; λmax 293, ε=15,450.

By analogous procedure the following compounds were obtained:

N-deformyl-N-[N-methyl-4-[N,N-bis(2-chloroethylamino)]pyrrole-2-carboxamido]Distamycin A.-hydrochloride;

3-[N-methyl-4-[N-methyl-4-[N,N-bis(2-chloroethylamino)]pyrrole-2-carboxamido]pyrrole-2-carboxamido]propyl-dimethylamine hydrochloride;

3-[N-methyl-4-[N-methyl-4-[N-methyl-4-[N,N-bis(2-chloroethylamino)]pyrrole-2-carboxamido]pyrrole-2-carboxamido]propyl-dymethylamine hydrochloride.

3-[N-methyl-4-[N-methyl-4-[N-methyl-4[N-methyl-4[N,N-bis(2-chloroethylamino]pyrrole-2-carboxamido]pyrrole-2-carboxamido] pyrrole-2-carboxamido]pyrrole-2-carboxamido]propyl-dimethylaminehydrochloride.

EXAMPLE 5

To an ice-cooled solution of β-[N-methyl-4-(N-methyl-4-aminopyrrole-2-carboxamido)pyrrole-2-carboxamido]propionamidine dihydrochloride (0.404 g) in 5 ml of DMF and 320 mg of 2,4,5-trichlorophenyl-N-methyl-N-nitrosocarbamate [prepared according to J. Med. Chem. 25, 178 (1982)], a solution of diisopropylethylamine (0.164 ml) in 8 ml of DMF was added dropwise. The resulting solution was stirred 1 hour at 0° C. The reaction mixture was concentrated under vacuum and the residue was purified by column chromatography to yield 251 mg of β-[N-methyl-4-[N-methyl-4-(3-methyl-3-nitrosoureido)pyrrole-2-carboxamido]pyrrole-2-carboxamido]propionamidine hydrochloride.

| U.V.(EtOH 95%) | |
|---|---|
| λmax | ε |
| 241 | 21,611 |
| 293 | 28,207 |

I.R. (KBr): $\nu cm^{-1}$ 3500–2800; 2500–2200; 1450; 970; 650.

N.M.R. (DMS0-$d_6$) δ: 2.59 (2H, m); 3.15 (3H, s); 3.48 (2H, m); 3.79 (3H, s); 3.85 (3H, s); 7.01–7.31 (4H, m); 8.61 (2H, br); 8.97 (2H, br); 9.91 (2H, b); 10.61 (1H, bs).

By analogous procedure the following compounds were obtained:

β-[N-methyl-4-[N-methyl-4-[3-(2-chloroethyl)-3-nitrosoureido]-pyrrole-2-carboxamido]pyrrole-2-carboxamido]propionamidine hydrochloride;

3-[N-methyl-4-[N-methyl-4-[3-methyl-3-nitrosoureido]-pyrrole-2-carboxamido]pyrrole-2-carboxamido]propyl-dimethylamine hydrochloride;

3-[N-methyl-4-[N-methyl-3-[3-(2-chloroethyl)-3-nitrosoureido]pyrrole-2-carboxamido]pyrrole-2-carboxamido]propyl-dimethylamine hydrochloride;

3-[N-methyl-4-[N-methyl-4-[N-methyl-4-(3-methyl-3-nitrosoureido)pyrrole-2-carboxamido]pyrrole-2-carboxamido]propyl-dimethylamine hydrochloride;

3-[N-methyl-4-[N-methyl-4-[N-methyl-4-[3-(2-chloroethyl)-3-nitrosoureido]pyrrole-2-carboxamido]pyrrole-2-carboxamido]propyl-dimethylamine hydrochloride;

N-deformyl-N-[N-methyl-4-(3-methyl-3-nitrosoureido)-pyrrole-2-carboxamido]Distamycin A.hydrochloride;

N-deformyl-N-[N-methyl-4-[3-(2-chloroethyl)-3-nitrosoureido]pyrrole-2-carboxamido]Distamycin A. hydrochloride;

3-[N-methyl-4-[N-methyl-4-[N-methyl-4-[N-methyl-4(3-methyl-3-nitrosoureido)pyrrole-2-carboxamido]-pyrrole-2-carboxamido]pyrrole-2-carboxamido]pyrrole-2-carboxamido]propyl-dimethylamine hydrochloride;

3-[N-methyl-4-[N-methyl-4-[N-methyl-4-[N-methyl-4[3-(2-chloroethyl)-3-nitrosoureido]pyrrole-2-carboxamido]pyrrole-2-carboxamido]pyrrole-2-carboxamido]propyl-dimethylamine hydrochloride;

N.M.R. (DMSO-$d_6$/CDCl$_3$) δ: 1.90 (2H, m); 2.60 (6H, s); 2.85 (2H, t); 3.15–4.00 (6H, m); 4.22 (2H, t); 6.80–7.30 (8H, m); 8.00 (1H, t); 9.63 (1H, bs); 9.70 (1H, s); 9.77 (1H, s); 10.48 (1H, s);

β-[N-methyl-4-[N-methyl-4-(oxiranecarboxamido)pyrrole-2-carboxamido]pyrrole-2-carboxamido]propionamidine hydrochloride;

3-[N-methyl-4-[N-methyl-4-(oxiranecarboxamido)pyrrole-2-carboxamido]pyrrole-2-carboxamido]propyl-dimethylamine hydrochloride;

3-[N-methyl-4-[N-methyl-4-[N-methyl-4-(oxiranecarboxamido)pyrrole-2-carboxamido]pyrrole-2-carboxamido]pyrrole-2-carboxamido]propyl-dimethylamine.

EXAMPLE 6

To a solution of (2R,3R)-3-methyl-orixane-carboxylic acid (765 mg) in dry THF (20 ml), cooled to −20° C., N-methylmorpholine (0.825 ml) and than pivaloyl chloride (0.920 ml) were added. The resulting suspension was stirred at −20° C. for 20 minutes, then the whole was added to a cooled solution of 2.6 g of 3-[N-methyl-4-[N-methyl-4-[N-methyl-4-aminopyrrole-2-carboxamido]pyrrole-2-carboxamido]pyrrole-2-carboxamido]propyl-dimethylamino dihydrochloride in DMF (50 ml) and NaHCO$_3$ (0.4 g). The mixture was stirred for 30 minutes at 0° C., and then for 4 hours at room temperature. Solvents were evaporated in vacuum to dryness, and the residue chromatographed on SiO$_2$ (solvent CHCl$_3$ 100/CH$_3$OH 100/HCl$_{2N}$ 1) to yield 1.4 g of 3-[N-methyl-4-[N-methyl-4-[N-methyl-4-[3-methyl-(2R,3R)oxiranecarboxamido]pyrrole-2-carboxamido]-pyrrole-2-carboxamido]pyrrole-2-carboxamido]propyl-dimethylamino hydrochloride.

N.M.R. (DMSO-$d_6$) δ: 1.25 (3H, d); 3.3 (1H, m); 3.60 (1H, d); [J=4.7H$_2$(cis)].

By analogous procedure the following compounds were obtained:

N-deformyl-N-[N-methyl-4-(oxiranecarboxamido)pyrrole-2-carboxamido]Distamycin A.hydrochloride;

3-[N-methyl-4-[N-methyl-4-[N-methyl-4-[N-methyl-4-(oxiranecarboxamido)pyrrole-2-carboxamido]pyrrole-2-carboxamido]pyrrole-2-carboxamido]pyrrole-2-carboxamido]propyl-dimethylamine hydrochloride;

β-[N-methyl-4-[N-methyl-4-(cyclopropylcarboxamido)pyrrole-2-carboxamido]pyrrole-2-carboxamido]propionamidine hydrochloride;

3-[N-methyl-4-[N-methyl-4-(cyclopropylcarboxamido)-pyrrole-2-carboxamido]pyrrole-2-carboxamido]propyl-dimethylamine hydrochloride;

3-[N-methyl-4-[N-methyl-4-[N-methyl-4-(cyclopropylcarboxamido)pyrrole-2-carboxamido]pyrrole-2-carboxamido]pyrrole-2-carboxamido]propyl-dimethylamine hydrochloride;

N-deformyl-N-[N-methyl-4-(cyclopropylcarboxamido)pyrrole-2-carboxamido]Distamycin A.hydrochloride;

3-[N-methyl-4-[N-methyl-4-[N-methyl-4-[N-methyl-4-(cyclopropylcarboxamido)pyrrole-2-carboxamido]-pyrrole-2-carboxamido]pyrrole-2-carboxamido]pyrrole-2-carboxamido]propyl-dimethylamine hydrochloride;

β-[N-methyl-4-[N-methyl-4-(3-methyloxiranecarboxamido)pyrrole-2-carboxamido]pyrrole-2-carboxamido]propionamidine hydrochloride;

3-[N-methyl-4-[N-methyl-4-(3-methyloxiranecarboxamido)pyrrole-2-carboxamido]pyrrole-2-carboxamido]propyl-dimethylamine hydrochloride;

3-[N-methyl-4-[N-methyl-4-[N-methyl-4-(3-methyloxiranecarboxamido)pyrrole-2-carboxamido]pyrrole-2-carboxamido]pyrrole-2-carboxamido]propyl-dimethylamine hydrochloride;

N-deformyl-N-[N-methyl-4-(3-methyloxiranecarboxamido)pyrrole-2-carboxamido]Distamycin A.hydrochloride;

3-[N-methyl-4-[N-methyl-4-[N-methyl-4-[N-methyl-4-(3-methyloxiranecarboxamido)pyrrole-2-carboxamido]pyrrole-2-carboxamido]pyrrole-2-carboxamido]pyrrole-2-carboxamido]propyl-dimethylamine hydrochloride;

β-[N-methyl-4-[N-methyl-4-(2-chloroethylcarboxamido)pyrrole-2-carboxamido]pyrrole-2-carboxamido]propionamidine hydrochloride;

3-[N-methyl-4-[N-methyl-4-(2-chloroethylcarboxamido)pyrrole-2-carboxamido]pyrrole-2-carboxamido]propyl-dimethylamine hydrochloride;

3-[N-methyl-4-[N-methyl-4-[N-methyl-4-(2-chloroethylcarboxamido)pyrrole-2-carboxamido]pyrrole-2-carboxamido]pyrrole-2-carboxamido]propyl-dimethylamine hydrochloride;

N-deformyl-N-[N-methyl-4-(2-chloroethylcarboxamido)pyrrole-2-carboxamido]Distamycin A.hydrochloride;

3-[N-methyl-4-[N-methyl-4-[N-methyl-4-[N-methyl-4-(2-chloroethylcarboxamido)pyrrole-2-carboxamido]pyrrole-2-carboxamido]pyrrole-2-carboxamido]pyrrole-2-carboxamido]propyl-dimethylamine hydrochloride;

β-[N-methyl-4-[N-methyl-4-[1-(aziridine)carboxamido]pyrrole-2-carboxamido]pyrrole-2-carboxamido]propionamidine hydrochloride;

3-[N-methyl-4-[N-methyl-4-[1-(aziridine)carboxamido]pyrrole-2-carboxamido]pyrrole-2-carboxamido]propyl-dimethylamine hydrochloride;

3-[N-methyl-4-[N-methyl-4-[N-methyl-4-[1-(aziridine)carboxamido]pyrrole-2-carboxamido[pyrrole-2-carboxamido]pyrrole-2-carboxamido]propyl-dimethylamine hydrochloride;

N-deformyl-N-[N-methyl-4-[1-(aziridine)carboxamido]pyrrole-2-carboxamido]Distamycin A.hydrochloride;

3-[N-methyl-4-[N-methyl-4-[N-methyl-4-[N-methyl-4-[1-(aziridine)carboxamido]pyrrole-2-carboxamido]pyrrole-2-carboxamido]pyrrole-2-carboxamido]pyrrole-2-carboxamido]propyl-dimethylamine hydrochloride.

We claim:

1. A compound of formula (I)

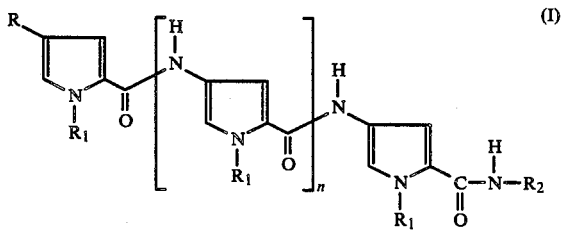

wherein
n is zero or an integer of 1 to 3;
R is
(a) —NHR$_3$, wherein R$_3$ is (a') —CON(NO)R$_4$, in which R$_4$ is C$_1$-C$_4$ alkyl either unsubstituted or substituted by halogen; or (b') —CO(CH$_2$)$_m$—R$_5$, in which R$_5$ is halogen, oxiranyl, methyloxiranyl, aziridinyl, a group

or a group

and m is zero or an integer of 1 to 4; or (b)

wherein either R$_6$ and R$_7$ are the same and are each oxiranemethyl, aziridinemethyl, or C$_2$-C$_4$ alkyl 2-substituted by halogen or by a group —OSO$_2$R$_8$ wherein R$_8$ is C$_1$-C$_4$ alkyl or pheynl, or one of R$_6$ and R$_7$ is hydrogen and the other is as defined above;

each group R$_1$ is, independently, hydrogen or C$_1$-C$_4$ alkyl;

R$_2$ is a C$_1$-C$_6$ alkyl group terminating with (i) a basic moiety chosen from an amino group, a mono- or di-C$_1$-C$_6$ alkylamino group, an amidino group, a group

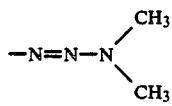

imidazolyl, imidazolinyl, tetrahydropyrimidinyl and oxazolidinyl; or (ii) a carboxy group; or (iii) a free hydroxy group —OH or a glycosilated hydroxy group —OD wherein D is a glucose, mannose or ribose sugar moiety or the daunosamine aminosugar moiety with the proviso that n is different from one when R$_2$ is

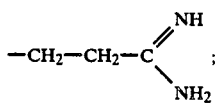

and the pharmaceutically acceptable salts thereof.

2. A compound of formula (I), according to claim 1 wherein, subject to the proviso of claim 1,
n is zero, 1 or 2;
R is —NHR$_3$ wherein R$_3$ is
(a') —CON(NO)R$_4$ wherein R$_4$ is C$_1$-C$_4$ alkyl substituted by halogen or
(b') —CO(CH$_2$)$_m$—R$_5$ wherein R$_5$ is halogen, oxyranyl, 1-aziridinyl, a group

or a group

and m is zero, 1 or 2;

each group $R_1$ is, independently, $C_1$-$C_4$ alkyl; $R_2$ is a $C_1$-$C_6$ alkyl group terminating with a basic moiety chosen from an amino group, a mono- or di-$C_1$-$C_6$ alkyl-amino group; an amidino group, a group

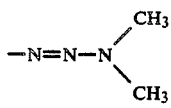

or a nitrogen containing heteromonocyclic ring selected from the group consisting of imidazolyl, imidazolinyl, tetrahydropyrimidinyl and oxazolidinyl, and the salts thereof with pharmaceutically acceptable acids.

3. A compound of formula (I), according to claim 1 wherein, subject to the proviso of claim 1, n is zero, 1 or 2;

R is

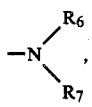

wherein $R_6$ and $R_7$ are the same and are each oxiranemethyl, 1-aziridinemethyl, or a $C_2$-$C_4$ alkyl group 2-substituted by halogen or by a group —O—$SO_2R_8$ wherein $R_8$ is $C_1$-$C_4$ alkyl;

each group $R_1$ is, independently, $C_1$-$C_4$ alkyl; $R_2$ is a $C_1$-$C_6$ alkyl group terminating with a basic moiety chosen from an amino group, a mono- or a di-$C_1$-$C_6$ alkylamino group, an amidino group, a group

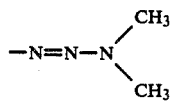

or a nitrogen containing heteromonocyclic ring selected from the group consisting of imidazolyl, imidazolinyl, tetrahydropyrimidinyl and oxazolidinyl, and the salts thereof with pharmaceutically acceptable acids.

4. A compound of formula (I) as defined in claim 1 selected from the group consisting of:

β-[N-methyl-4-[N-methyl-4-(3-methyl-3-nitrosoureido)pyrrole-2-carboxamido]pyrrole-2-carboxamido]propionamidine;

β-[N-methyl-4-[N-methyl-4-[3-(2-chloroethyl)-3-nitrosoureido]pyrrole-2-carboxamido]pyrrole-2-carboxamido]propionamidine;

3-[N-methyl-4-[N-methyl-4-[3-methyl-3-nitrosoureido]pyrrole-2-carboxamido]pyrrole-2-carboxamido]propyl-dimethylamine;

3-[N-methyl-4-[N-methyl-3-[3-(2-chloroethyl)-3-nitrosoureido]pyrrole-2-carboxamido]pyrrole-2-carboxamido]propyl-dimethylamine;

3-[N-methyl-4-[N-methyl-4-[N-methyl-4-(3-methyl-3-nitrosoureido)pyrrole-2-carboxamido]pyrrole-2-carboxamido]pyrrole-2-carboxamido]propyl-dimethylamine;

3-[N-methyl-4-[N-methyl-4-[N-methyl-4-[3-(2-chloroethyl)-3-nitrosoureido]pyrrole-2-carboxamido]pyrrole-2-carboxamido]pyrrole-2-carboxamido]propyl-dimethylamine;

N-deformyl-N-[N-methyl-4-(3-methyl-3-nitrosoureido)-pyrrole-2-carboxamido]Distamycin A;

N-deformyl-N-[N-methyl-4-[3-(2-chloroethyl)-3-nitrosoureido]pyrrole-2-carboxamido]Distamycin A;

3-[N-methyl-4-[N-methyl-4-[N-methyl-4-[N-methyl-4(3-methyl-3-nitrosoureido)pyrrole-2-carboxamido]pyrrole-2-carboxamido]pyrrole-2-carboxamido]pyrrole-2-carboxamido]propyl-dimethylamine;

3-[N-methyl-4-[N-methyl-4-[N-methyl-4-[N-methyl-4[3-(2-chloroethyl)-3-nitrosoureido]pyrrole-2-carboxamido]pyrrole-2-carboxamido]pyrrole-2-carboxamido]pyrrole-2-carboxamido]propyl-dimethylamine;

β-[N-methyl-4-[N-methyl-4-(oxiranecarboxamido)pyrrole-2-carboxamido]pyrrole-2-carboxamido]propionamidine;

3-[N-methyl-4-[N-methyl-4-(oxiranecarboxamido)pyrrole-2-carboxamido]pyrrole-2-carboxamido]propyl-dimethylamine;

3-[N-methyl-4-[N-methyl-4-[N-methyl-4-(oxiranecarboxamido)pyrrole-2-carboxamido]pyrrole-2-carboxamido]pyrrole-2-carboxamido]propyl-dimethylamine;

N-deformyl-N-[N-methyl-4-(oxiranecarboxamido)pyrrole-2-carboxamido]Distamycin A;

3-[N-methyl-4-[N-methyl-4-[N-methyl-4-[N-methyl-4-(oxiranecarboxamido)pyrrole-2-carboxamido]pyrrole-2-carboxamido]pyrrole-2-carboxamido]pyrrole-2-carboxamido]propyl-dimethylamine;

β-[N-methyl-4-[N-methyl-4-(3-methyloxiranecarboxamido)pyrrole-2-carboxamido]pyrrole-2-carboxamido]propionamidine;

3-[N-methyl-4-[N-methyl-4-(3-methyloxiranecarboxamido)pyrrole-2-carboxamido]pyrrole-2-carboxamido]propyl-dimethylamine;

3-[N-methyl-4-[N-methyl-4-[N-methyl-4-(3-methyloxiranecarboxamido)pyrrole-2-carboxamido]pyrrole-2-carboxamido]pyrrole-2-carboxamido]propyl-dimethylamine;

N-deformyl-N-[N-methyl-4-(3-methyloxiranecarboxamido)pyrrole-2-carboxamido]Distamycin A;

3-[N-methyl-4-[N-methyl-4-[N-methyl-4-[N-methyl-4-(3-methyloxiranecarboxamido)pyrrole-2-carboxamido]pyrrole-2-carboxamido]pyrrole-2-carboxamido]pyrrole-2-carboxamido]propyl-dimethylamine;

β-[N-methyl-4-[N-methyl-4-(2-chloroethylcarboxamido)pyrrole-2-carboxamido]pyrrole-2-carboxamido]propionamidine;

3-[N-methyl-4-[N-methyl-4-(2-chloroethylcarboxamido)pyrrole-2-carboxamido]pyrrole-2-carboxamido]propyl-dimethylamine;

3-[N-methyl-4-[N-methyl-4-[N-methyl-4-(2-chloroethylcarboxamido)pyrrole-2-carboxamido]pyrrole-2- carboxamido]pyrrole-2-carboxamido]propyl-dimethylamine;

N-deformyl-N-[N-methyl-4-(2-chloroethylcarboxamido)pyrrole-2-carboxamido]Distamycin A;

3-[N-methyl-4-[N-methyl-4-[N-methyl-4-(2-chloroethylcarboxamido)pyrrole-2-carboxamido]-pyrrole-2-carboxamido]pyrrole-2-carboxamido]pyrrole-2-carboxamido]propyl-dimethylamine;

β-[N-methyl-4-[N-methyl-4-[1-(aziridine)carboxamido]pyrrole-2-carboxamido]pyrrole-2-carboxamido]propionamidine;

3-[N-methyl-4-[N-methyl-4-[1-(aziridine)carboxamido]-pyrrole-2-carboxamido]pyrrole-2-carboxamido]propyl-dimethylamine;

3-[N-methyl-4-[N-methyl-4-[N-methyl-4-[1-(aziridine)-carboxamido]pyrrole-2-carboxamido]pyrrole-2-carboxamido]pyrrole-2-carboxamido]propyl-dimethylamine;

N-deformyl-N-[N-methyl-4-[1-(aziridine)carboxamido]-pyrrole-2-carboxamido]Distamycin A;

3-[N-methyl-4-[N-methyl-4-[N-methyl-4-[N-methyl-4-[1-(aziridine)carboxamido]pyrrole-2-carboxamido]-pyrrole-2-carboxamido]pyrrole-2-carboxamido]pyrrole-2-carboxamido]propyl-dimethylamine;

β-[N-methyl-4-[N-methyl-4-[N,N-bis(2-chloroethylamino)]pyrrole-2-carboxamido]pyrrole-2-carboxamido]propionamidine;

3-[N-methyl-4-[N-methyl-4-[N,N-bis(2-chloroethylamino)]pyrrole-2-carboxamido]pyrrole-2-carboxamido]propyl-dimethylamine;

3-[N-methyl-4-[N-methyl-4-[N-methyl-4-[N,N-bis(-chloroethylamino)]pyrrole-2-carboxamido]pyrrole-2-carboxamido]pyrrole-2-carboxamido]propyl-dimethylamine;

N-deformyl-N-[N-methyl-4-[N,N-bis(2-chloroethylamino)]pyrrole-2-carboxamido]Distamycin A;

3-[N-methyl-4-[N-methyl-4-[N-methyl-4-[N-methyl-4-[N,N-bis(2-chloroethylamino)]pyrrole-2-carboxamido]pyrrole-2-carboxamido]pyrrole-2-carboxamido]pyrrole-2-carboxamido]propyl-dimethylamine.

5. A hydrochloric acid salt of a compound of formula (I) as claimed in claim 4.

6. An antiviral or antitumor pharmaceutical composition containing a suitable carrier and/or diluent and, as an active principle an effective amount of a compound of formula (I) according to claim 1 or a pharmaceutically acceptable salt thereof.

* * * * *